(12) United States Patent
Minick et al.

(10) Patent No.: US 8,689,971 B2
(45) Date of Patent: *Apr. 8, 2014

(54) CONTACT LENS PACKAGING SOLUTIONS

(75) Inventors: Kasey Jon Minick, Cumming, GA (US);
Fiona Patricia Carney, Stone Mountain, GA (US); Karen Belinda Sentell, Alpharetta, GA (US); George Edward Minno, Windham, NH (US)

(73) Assignee: Novartis AG, Basel (CH)

( * ) Notice: Subject to any disclaimer, the term of this patent is extended or adjusted under 35 U.S.C. 154(b) by 1156 days.

This patent is subject to a terminal disclaimer.

(21) Appl. No.: 12/229,771

(22) Filed: Aug. 27, 2008

(65) Prior Publication Data

US 2009/0057164 A1  Mar. 5, 2009

Related U.S. Application Data

(60) Provisional application No. 60/969,337, filed on Aug. 31, 2007.

(51) Int. Cl.
*A45C 11/04* (2006.01)
*B65B 3/00* (2006.01)
*B65B 55/02* (2006.01)
*A61L 12/00* (2006.01)

(52) U.S. Cl.
USPC ........................ 206/5.1; 53/425; 53/475

(58) Field of Classification Search
USPC .................................................. 424/400
See application file for complete search history.

(56) References Cited

U.S. PATENT DOCUMENTS

| | | | |
|---|---|---|---|
| 3,549,747 A | 12/1970 | Krezanoski et al. | 424/78 |
| 3,639,576 A | 2/1972 | Kaspar et at | 424/78 |
| 3,882,036 A | 5/1975 | Krezanoski et al. | 252/106 |
| 4,013,576 A | 3/1977 | Loshaek | 134/42 |
| 4,287,175 A | 9/1981 | Katz | 424/78 |
| 4,323,467 A | 4/1982 | Fu | 252/106 |
| 4,409,205 A | 10/1983 | Shively | 424/78 |
| 4,440,662 A | 4/1984 | Tsuzuki et al. | 252/106 |
| 4,500,441 A | 2/1985 | Tanaka et al. | 252/89.1 |
| 4,529,535 A | 7/1985 | Sherman | 252/106 |
| 4,551,461 A | 11/1985 | Sherman | 514/275 |
| 4,560,491 A | 12/1985 | Sherman | 252/106 |
| 4,626,292 A | 12/1986 | Sherman | 134/26 |
| 4,746,514 A | 5/1988 | Warne | 424/445 |
| 4,748,189 A | 5/1988 | Su et al. | 514/781 |
| 4,783,488 A | 11/1988 | Ogunbiyi et al. | 514/635 |
| 4,786,436 A | 11/1988 | Ogunbiyi et al. | 252/352 |
| 4,808,239 A | 2/1989 | Schaefer et al. | 134/42 |
| 5,036,971 A | 8/1991 | Seden et al. | 206/5.1 |
| 5,141,665 A | 8/1992 | Sherman | 252/106 |
| 5,157,093 A | 10/1992 | Harisiades et al. | 527/301 |
| 5,198,477 A | 3/1993 | vonderHaegen et al. | 523/106 |
| 5,260,001 A | 11/1993 | Nandu et al. | 264/2.1 |
| 5,310,429 A | 5/1994 | Chou et al. | 134/6 |
| 5,322,667 A | 6/1994 | Sherman | 422/28 |
| 5,364,601 A | 11/1994 | Salpekar | 422/28 |
| 5,382,599 A | 1/1995 | Rupp et al. | 514/547 |
| 5,405,878 A | 4/1995 | Ellis et al. | 422/28 |
| 5,500,144 A | 3/1996 | Potini et al. | 253/174.15 |
| 5,604,189 A | 2/1997 | Zhang et al. | 510/112 |
| 5,605,661 A * | 2/1997 | Asgharian et al. | 422/28 |
| 5,711,823 A | 1/1998 | Ellis et al. | 134/42 |
| 5,712,356 A | 1/1998 | Bothe et al. | 526/264 |
| 5,726,733 A | 3/1998 | Lai et al. | 351/160 |
| 5,731,087 A | 3/1998 | Fan et al. | 428/412 |
| 5,773,396 A | 6/1998 | Zhang et al. | 510/115 |
| 5,800,412 A | 9/1998 | Zhang et al. | 604/280 |
| 5,800,807 A | 9/1998 | Hu et al. | 424/78 |
| 5,807,636 A | 9/1998 | Sheu et al. | 428/403 |
| 5,837,377 A | 11/1998 | Sheu et al. | 428/412 |
| 5,872,086 A | 2/1999 | Ellis et al. | 510/112 |
| 5,882,687 A | 3/1999 | Park et al. | 424/682 |
| 5,942,558 A | 8/1999 | Korb | 523/106 |
| 5,985,629 A | 11/1999 | Aaslyng et al. | 435/174 |
| 5,998,498 A | 12/1999 | Vanderlaan et al. | 523/107 |
| 6,037,328 A | 3/2000 | Hu et al. | 514/23 |
| 6,121,327 A | 9/2000 | Tsuzuki et al. | 514/642 |
| 6,136,850 A | 10/2000 | Park et al. | 514/458 |
| 6,193,369 B1 | 2/2001 | Valint, Jr. et al. | 351/160 |
| 6,207,628 B1 | 3/2001 | Soyer et al. | 510/112 |
| 6,258,591 B1 | 7/2001 | Yoneda et al. | 435/264 |
| 6,274,133 B1 | 8/2001 | Hu et al. | 424/78.04 |
| 6,338,847 B1 | 1/2002 | Thomas | 424/94.2 |
| 6,348,507 B1 | 2/2002 | Heiler et al. | 514/769 |
| 6,428,839 B1 | 8/2002 | Kunzler et al. | 427/2.1 |
| 6,440,366 B1 | 8/2002 | Salpekar et al. | 422/40 |
| 6,482,799 B1 | 11/2002 | Tuse et al. | 514/14 |
| 6,528,048 B1 | 3/2003 | Koike et al. | 424/78.17 |
| 6,531,432 B2 | 3/2003 | Molock et al. | 510/112 |
| 6,617,291 B1 | 9/2003 | Smith | 510/112 |
| 6,634,748 B1 | 10/2003 | Vanderlaan et al. | 351/177 |
| 6,686,330 B2 | 2/2004 | Jordan et al. | 510/475 |
| 6,699,435 B2 | 3/2004 | Salpekar et al. | 422/40 |
| 6,702,983 B2 | 3/2004 | Hu et al. | 422/1 |
| 6,805,836 B2 | 10/2004 | Salamone et al. | 422/1 |
| 6,815,074 B2 | 11/2004 | Aguado et al. | 428/447 |
| 6,822,016 B2 | 11/2004 | McCabe et al. | 523/107 |

(Continued)

FOREIGN PATENT DOCUMENTS

EP  0 315 836  10/1988
EP  1 187 873 B  9/2004

(Continued)

*Primary Examiner* — Janet Epps-Smith
*Assistant Examiner* — Audrea Buckley
(74) *Attorney, Agent, or Firm* — Jian Zhou

(57) ABSTRACT

The present invention relates to improved contact lens products which not only have initial insertion comfort. The contact lens product of the invention comprises a soft hydrogel contact lens immersed and autoclaved in a packaging solution including a low molecular weight polyethylene glycol (PEG) (or glycerin) and a homopolymer or copolymer of vinylpyrrolidone. The present invention also provides methods for making contact lens products of the invention.

18 Claims, 1 Drawing Sheet

(56) References Cited

U.S. PATENT DOCUMENTS

| | | | |
|---|---|---|---|
| 6,867,172 B2 | 3/2005 | Alvarez et al. | 510/112 |
| 6,926,965 B2 | 8/2005 | Qiu et al. | 428/411.1 |
| 7,037,469 B2 | 5/2006 | Hu et al. | 422/28 |
| 7,247,270 B2 | 7/2007 | Hu et al. | 422/28 |
| 2002/0018732 A1 | 2/2002 | Hung et al. | 422/28 |
| 2002/0071789 A1 | 6/2002 | Molock et al. | 422/112 |
| 2002/0115578 A1 | 8/2002 | Groemminger | 510/112 |
| 2002/0182315 A1 | 12/2002 | Heiler et al. | 427/162 |
| 2003/0052424 A1 | 3/2003 | Turner et al. | 264/1.32 |
| 2003/0095230 A1 | 5/2003 | Neeley et al. | 351/159 |
| 2003/0096717 A1 | 5/2003 | Xia et al. | 510/112 |
| 2003/0125498 A1 | 7/2003 | McCabe et al. | 528/25 |
| 2003/0129083 A1 | 7/2003 | Graham et al. | 422/42 |
| 2003/0130144 A1 | 7/2003 | Alvarez et al. | 510/112 |
| 2003/0162862 A1 | 8/2003 | McCabe et al. | 523/106 |
| 2004/0028645 A1 | 2/2004 | Chowham | 424/78.27 |
| 2004/0119176 A1 | 6/2004 | Xia et al. | 264/1.32 |
| 2004/0120916 A1 | 6/2004 | Huth | 424/661 |
| 2004/0120982 A1 | 6/2004 | Diana et al. | 424/420 |
| 2004/0137079 A1 | 7/2004 | Cook et al. | 424/662 |
| 2004/0142829 A1 | 7/2004 | Tsao et al. | 510/112 |
| 2005/0006255 A1 | 1/2005 | Peck et al. | 206/5.1 |
| 2005/0047270 A1 | 3/2005 | Wood et al. | 366/170.3 |
| 2005/0117112 A1 | 6/2005 | Nayiby et al. | 351/160 |
| 2005/0119141 A1 | 6/2005 | Quenville et al. | 510/112 |
| 2005/0154080 A1 | 7/2005 | McCabe et al. | 523/107 |
| 2005/0260280 A1 | 11/2005 | Cook et al. | 424/661 |
| 2005/0266089 A1 | 12/2005 | Cook et al. | 424/488 |
| 2006/0039939 A1* | 2/2006 | Lai et al. | 424/401 |
| 2006/0063852 A1 | 3/2006 | Iwata et al. | 523/106 |
| 2006/0073185 A1* | 4/2006 | Jani et al. | 424/427 |
| 2006/0074208 A1 | 4/2006 | Laredo | 526/279 |
| 2006/0094643 A1 | 5/2006 | Svirkin et al. | 514/8 |
| 2006/0135381 A1 | 6/2006 | Hu et al. | 520/112 |
| 2006/0251696 A1 | 11/2006 | Winterton et al. | 424/422 |
| 2007/0010595 A1 | 1/2007 | McCabe et al. | 523/106 |
| 2007/0195261 A1 | 8/2007 | Vogt et al. | 351/158 |

FOREIGN PATENT DOCUMENTS

| | | | | |
|---|---|---|---|---|
| GB | 1340516 | 11/1970 | | |
| GB | 1340518 | 11/1970 | | |
| KR | 1994-006102 | 7/1994 | | |
| KR | 1857301 A | 4/2005 | | |
| WO | WO 94/04028 | 3/1994 | | |
| WO | WO 94/09794 | 5/1994 | | |
| WO | WO 95/00615 | 1/1995 | | |
| WO | WO 95/00618 | 1/1995 | | |
| WO | WO 95/34327 | 12/1995 | | |
| WO | WO 97/20019 | 6/1997 | | |
| WO | WO 00/02937 | 1/2000 | | |
| WO | WO 00/37048 | 6/2000 | | |
| WO | WO 01/20997 A1 | 3/2001 | | |
| WO | WO 01/27174 A1 | 4/2001 | | |
| WO | WO 01/34312 A1 | 5/2001 | | |
| WO | WO 01/70837 A1 | 9/2001 | | |
| WO | WO 02/38161 A1 | 5/2002 | | |
| WO | WO2004/054629 A1 * | 7/2004 | | 424/400 |
| WO | WO 2004/055148 A1 | 7/2004 | | |
| WO | WO 2004/060099 A2 | 7/2004 | | |
| WO | WO 2004/091438 A2 | 10/2004 | | |
| WO | WO 2005/011966 A1 | 2/2005 | | |
| WO | WO 2005/092987 A1 | 10/2005 | | |
| WO | WO2006/009101 A1 | 1/2006 | | |
| WO | WO 2006/038080 A2 | 4/2006 | | |
| WO | WO 2006/061990 A1 | 6/2006 | | |
| WO | WO 2006/088758 A2 | 8/2006 | | |

\* cited by examiner

CONTACT LENS PACKAGING SOLUTIONS

This application claims the benefit under 35 USC §119 (e) of U.S. provisional application No. 60/969,337 filed Aug. 31, 2007, incorporated by reference in its entirety.

The present invention relates to improved contact lens products which not only have initial insertion comfort, in particular, to a packaging solution for autoclaving and storing contact lenses.

BACKGROUND OF THE INVENTION

One long felt need in the contact lens industry is to provide contact lenses which are comfortable for users to wear. One of the problems that contact lens users complain of most is initial discomfort (i.e., immediately after lens insertion). One of the approaches is to use soft contact lenses to alleviate to some extent the initial discomfort because of their relatively soft surfaces, but also to their pliability, which permits them to modify their shape somewhat with different eyes. Such approach requires a great effort in developing new materials and lens designs and may not be cost effective. Another approach is to apply directly eye drops of an ocular lubricant into the wearer's eye while the lens is being worn, in order to provide some relief to some extent, e.g., the initial discomfort of wearers, discomfort suffering from dry-eye effects, or end-of-day discomfort. But, eye drops are typically applied only after a lens wearer is already suffering discomfort and as such do not prevent the discomfort from happening. Recently, surfactants or lubricants are added in the lens packaging solution to ease to some extent initial discomfort and other symptoms (see, for example, U.S. Pat. Nos. 5,882,687, 5,942,558, 6,348,507, 6,440,366, 6,531,432, and 6,699,435; and Published PCT Patent Applications WO9720019 and WO2006/088758). In spite of the forgoing efforts, there are no commercially available contact lenses, especially extended-wear contact lenses (e.g., silicone hydrogel contact lenses), which can provide greatly-enhanced initial comfort. Therefore, there is still a need for cost-effective methods for making contact lens products which can provide initial insertion comfort to lens wearers.

SUMMARY OF THE INVENTION

The present invention, in one aspect, provides an ophthalmic product comprising a sealed and sterilized package which include a packaging solution and a soft hydrogel contact lens immersed in the packaging solution, wherein the packaging solution includes: a homopolymer or copolymer of vinylpyrrolidone, wherein the homopolymer or copolymer of vinylpyrrolidone is present in an amount sufficient to provide the packaging solution a viscosity of up to about 5.0 centipoises, preferably up to about 4.0 centipoises, even more preferably up to about 3.0 centipoises, most preferably from about 1.2 centipoises to about 2.5 centipoises at 25° C.; glycerin or a polyethylene glycol having an average molecular weight of about 600 daltons or less; an α-oxo-multi-acid or salt thereof in an amount sufficient to have a reduced susceptibility to oxidation degradation of the polyethylene glycol in the packaging solution; and one or more buffering agents in an amount sufficient to provide the solution a pH of from about 6.0 to 8.0, wherein the packaging solution has an osmolality of from about 200 to about 450 mOsm/kg.

The present invention, in another aspect, provides a process for making a soft contact lens capable of easing wearer's initial discomfort. The method of the invention comprises the steps of: a) packaging a hydrogel contact lens in a container containing a packaging solution, wherein the packaging solution comprises a homopolymer or copolymer of vinylpyrrolidone, wherein the homopolymer or copolymer of vinylpyrrolidone is present in an amount sufficient to provide the packaging solution a viscosity of up to about 5.0 centipoises, preferably up to about 4.0 centipoises, even more preferably up to about 3.0 centipoises, most preferably from about 1.2 centipoises to about 2.5 centipoises at 25° C.; glycerin or a polyethylene glycol having an average molecular weight of about 600 or less; an α-oxo-multi-acid or salt thereof in an amount sufficient to have a reduced susceptibility to oxidation degradation of the polyethylene glycol in the packaging solution; and one or more buffering agents in an amount sufficient to provide the solution a pH of from about 6.0 to 8.0, wherein the packaging solution has an osmolality of from about 200 to about 450 mOsm/kg; and b) sterilizing the hydrogel contact lens in the package to obtain the soft contact lens.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE INVENTION

Figure 1:
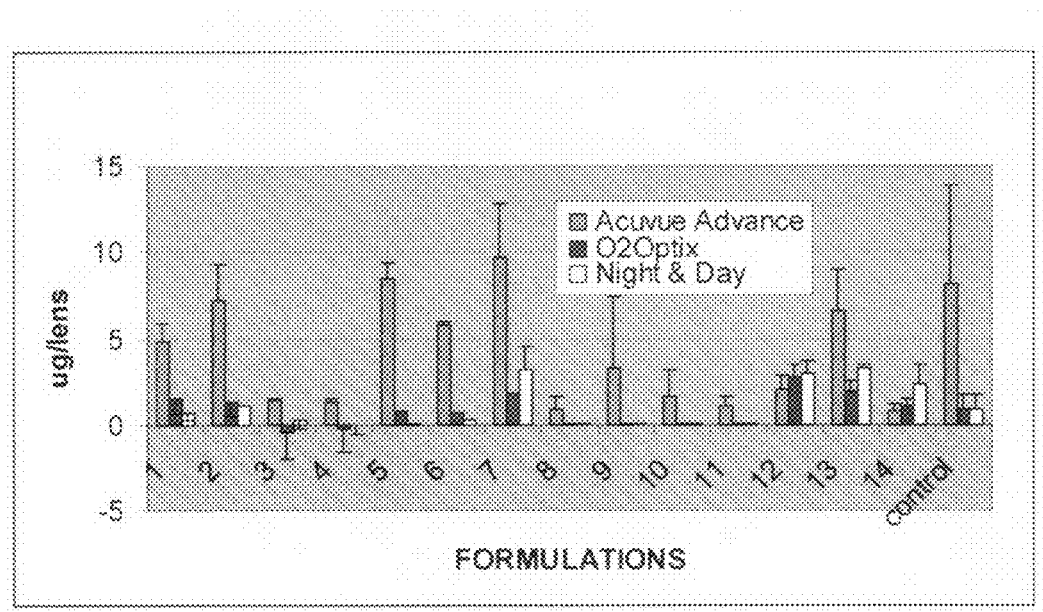
FIG. 1 shows effects of a packaging solution upon in vitro lipid fouling of commercially available silicone hydrogel lenses.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

A "hydrogel" refers to a polymeric material which can absorb at least 10 percent by weight of water when it is fully hydrated. A hydrogel material can be obtained by polymerization or copolymerization of at least one hydrophilic monomer in the presence of or in the absence of additional monomers and/or macromers or by crosslinking of a prepolymer.

A "silicone hydrogel" refers to a hydrogel obtained by copolymerization of a polymerizable composition comprising at least one silicone-containing vinylic monomer or at least one silicone-containing macromer or a silicone-containing prepolymer.

A "monomer" means a low molecular weight compound that can be polymerized actinically or thermally. Low molecular weight typically means average molecular weights less than 700 Daltons. In accordance with the invention, a monomer can be a vinylic monomer or a compound comprising two thiol groups. A compound with two thiol groups can participate in thiol-ene step-growth radical polymerization with a monomer with vinyl group to form a polymer. Step-growth radical polymerization can be used in making contact lenses, as described in a commonly-owned copending U.S. patent application No. 60/869,812 filed Dec. 13, 2006 (entitled "Production of Ophthalmic Devices Based on Photo-Induced Step Growth Polymerization", herein incorporated in reference in its entirety.

A "vinylic monomer", as used herein, refers to a low molecular weight compound that has an ethylenically unsaturated group and can be polymerized actinically or thermally. Low molecular weight typically means average molecular weights less than 700 Daltons.

The term "olefinically unsaturated group" or "ethylentically unsaturated group" is employed herein in a broad sense and is intended to encompass any groups containing at least one >C=C< group. Exemplary ethylenically unsaturated groups include without limitation acryloyl, methacryloyl, allyl, vinyl, styrenyl, or other C=C containing groups.

As used herein, "actinically" in reference to curing or polymerizing of a polymerizable composition or material means that the curing (e.g., crosslinked and/or polymerized) is performed by actinic irradiation, such as, for example, UV irradiation, ionized radiation (e.g. gamma ray or X-ray irradiation), microwave irradiation, and the like. Thermal curing or actinic curing methods are well-known to a person skilled in the art.

The term "fluid" as used herein indicates that a material is capable of flowing like a liquid.

A "hydrophilic monomer" refers to a monomer which can be polymerized actinically or thermally to form a polymer that is water-soluble or can absorb at least 10 percent by weight water.

A "hydrophobic monomer", as used herein, refers to a monomer which is polymerized actinically or thermally to form a polymer that is insoluble in water and can absorb less than 10 percent by weight water.

A "macromer" refers to a medium and high molecular weight compound which can be polymerized and/or crosslinked actinically or thermally. Medium and high molecular weight typically means average molecular weights greater than 700 Daltons. In accordance with the invention, a macromer comprises one or more ethylenically unsaturated groups and/or one or more thiol groups, which can participate in free radical chain growth polymerization or thiol-ene step-growth radical polymerization. Preferably, a macromer contains ethylenically unsaturated groups and can be polymerized actinically or thermally.

A "prepolymer" refers to a starting polymer which contains crosslinkable groups and can be cured (e.g., crosslinked and/or polymerized) actinically or thermally to obtain a crosslinked and/or polymerized polymer having a molecular weight much higher than the starting polymer. In accordance with the invention, a prepolymer comprises one or more ethylenically unsaturated groups and/or one or more thiol groups, which can participate in free radical chain growth polymerization or thiol-ene step-growth radical polymerization.

A "silicone-containing prepolymer" refers to a prepolymer which contains silicone and can be crosslinked upon actinic radiation or thermally to obtain a crosslinked polymer having a molecular weight much higher than the starting polymer.

"Polymer" means a material formed by polymerizing one or more monomers or macromers or by crosslinking one or more prepolymers.

"Molecular weight" of a polymeric material (including monomeric or macromeric materials), as used herein, refers to the number-average molecular weight unless otherwise specifically noted or unless testing conditions indicate otherwise.

"Visibility tinting" in reference to a lens means dying (or coloring) of a lens to enable the user to easily locate a lens in a clear solution within a lens storage, disinfecting or cleaning container. It is well known in the art that a dye and/or a pigment can be used in visibility tinting of a lens.

A "photoinitiator" refers to a chemical that initiates radical crosslinking/polymerizing reaction by the use of light. Suitable photoinitiators include, without limitation, benzoin methyl ether, diethoxyacetophenone, a benzoylphosphine oxide, 1-hydroxycyclohexyl phenyl ketone, Darocure® types, and Irgacure® types, preferably Darocure® 1173, and Irgacure® 2959.

A "thermal initiator" refers to a chemical that initiates radical crosslinking/polymerizing reaction by the use of heat energy. Examples of suitable thermal initiators include, but are not limited to, 2,2'-azobis(2,4-dimethylpentanenitrile), 2,2'-azobis(2-methylpropanenitrile), 2,2'-azobis(2-methylbutanenitrile), peroxides such as benzoyl peroxide, and the like. Preferably, the thermal initiator is 2,2'-azobis(isobutyronitrile) (AIBN).

In accordance with the invention, a packaging solution is ophthalmic safe. The term "ophthalmically safe" with respect to a packaging solution is meant that a contact lens immersed in the solution is safe for direct placement on the eye without rinsing, that is, the solution is safe and sufficiently comfortable for daily contact with the eye via a contact lens. An ophthalmically safe solution has a tonicity and pH that is compatible with the eye and comprises materials, and amounts thereof, that are non-cytotoxic according to international ISO standards and U.S. FDA regulations.

The term "compatible with the eye" means a solution that may be in intimate contact with the eye for an extended period of time without significantly damaging the eye and without significant user discomfort.

A "reduced susceptibility to oxidation degradation of the polyethylene glycol" means that the susceptibility to oxidative degradation of a polyethylene glycol in a solution containing an α-oxo-multi-acid or salt thereof after subject to a sterilization treatment is reduced (characterized by the amount of detectable formic acid and optionally other degradation by-products in a stabilized poly(oxyalkylene)-containing polymeric material being 80% or less, preferably 65% or less, more preferably 50% or less, of that detected in a solution without any α-oxo-multi-acid or salt thereof). The methods for determining formic acid and other by-products derived from oxidative degradation PEG-containing polymeric materials are described in a commonly-owned co-pending patent application (US patent application publication No. 2004/0116564 A1, incorporated herein in its entirety). Alternatively, a person skilled in the art knows how to analyze the oxidative degradation products of a PEG-containing polymeric material.

A "leachable polymeric lubricant" as used herein refer to a non-ionic hydrophilic polymer which is not covalently bound to but instead is associated with or entrapped in the polymer matrix of a contact lens and which can enhance surface wettability of a contact lens and/or the eye or reduce the frictional character of the contact lens surface.

The present invention is generally directed to a hydrogel contact lens capable of easing lens-wearer's initial discomfort. The present invention is partly based on the discovery that a lens packaging solution including a homopolymer or copolymer of vinylpyrrolidone and a low molecular weight polyethylene glycol (PEG) (or glycerin) can provide to a hydrogel contact lens, which is immersed and autoclaved in the packaging solution, with unexpected benefits of increased wettability, reduced friction, initial conditioning (by cushioning the lens), and/or reduced adherence of deposits onto the lens.

Although the inventors do not wish to be bound by any particular theory, it is believed that a low molecular weight PEG (or glycerin) and a homopolymer or copolymer of vinylpyrrolidone can have a synergetic effects on the initial comfort (at the time of inserting the lens). The homopolymer or copolymer with sufficiently larger molecular weight can form a cushion layer between the lens and the epithelium of the cornea without increasing substantially the viscosity of the packaging solution (i.e., above 5 centipoises at 25° C.). Incorporation of a low molecular weight PEG or glycerin in the cushion layer can increase the lubricity, wettability (characterized by water contact angle) and/or reduced friction of the cushion layer. This added cushioning is believed to provide a temporary lubricious layer that would allow the lens to settle gently on the eye with slight lubrication and improve initial insert comfort.

The present invention, in one aspect, provides an ophthalmic product comprising a seated and sterilized package which include a packaging solution and a soft hydrogel contact lens immersed in the packaging solution, wherein the packaging solution includes: a homopolymer or copolymer of vinylpyrrolidone, wherein the homopolymer or copolymer is present in an amount sufficient to provide the packaging solution a viscosity of up to about 5.0 centipoise, preferably up to about 4.0 centipoises, even more preferably up to about 3.0 centipoises, most preferably from about 1.2 centipoises to about 2.5 centipoises at 25° C.; glycerin or a polyethylene glycol having an average molecular weight of about 600 or less; and one or more buffering agents in an amount sufficient to provide the solution a pH of from about 6.0 to 8.0, wherein the packaging solution has an osmolality of from about 200 to about 450 mOsm/kg.

Lens packages (or containers) are well known to a person skilled in the art for autoclaving and storing a soft contact lens. Any lens packages can be used in the invention. Preferably, a lens package is a blister package which comprises a base and a cover, wherein the cover is detachably sealed to the base, wherein the base includes a cavity for receiving a sterile packaging solution and the contact lens.

Lenses are packaged in individual packages, sealed, and sterilized (e.g., by autoclave at about 120° C. or higher for at least 30 minutes) prior to dispensing to users. A person skilled in the art will understand well how to seal and sterilize lens packages.

In accordance with the invention, a soft hydrogel contact lens can be a conventional hydrogel contact lens (i.e., a non-silicone hydrogel lens) or preferably a silicone hydrogel contact lens.

A packaging solution of the invention is ophthalmically compatible and may be any water-based solution that is used for the storage of contact lenses. A packaging solution of the invention can be a saline solution, a buffered solution, and deionized water.

Any copolymers of vinylpyrrolidone and at least one hydrophilic monomer can be used in this invention. A preferred class of copolymers are the copolymers of vinyloyrrolidone and at least one amino-containing vinylic monomer. Examples of amino-containing vinylic monomers include without limitation alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, N-vinylalkylamide having 3-10 carbon atoms. Examples of preferred N-vinyl alkylamide include without limitation N-vinyl formaide, N-vinyl acetamide, N-vinyl isopropylamide, and N-vinyl-N-methyl acetamide.

Examples of preferred copolymers includes without limitation copolymers of vinylpyrrolidone and dimethylaminoethylmethacrylate. Such preferred copolymers are commercially available, e.g., Copolymer 845 and Copolymer 937 from ISP.

In accordance with the invention, a polyethylene glycol has a molecular weight of about 600 or less, most preferably from about 100 to about 500.

In a preferred embodiment of the invention, the packaging solution comprises an α-oxo-multi-acid or salt thereof in an amount sufficient to have a reduced susceptibility to oxidation degradation of the polyethylene glycol in the packaging solution. A commonly-owned co-pending patent application (US patent application publication No. 2004/0116564 A1, incorporated herein in its entirety) discloses that oxo-multi-acid or salt thereof can reduce the susceptibility to oxidative degradation of a PEG-containing polymeric material.

Exemplary α-oxo-multi-acids or biocompatible salts thereof include without limitation citric acid, 2-ketoglutaric acid, or malic acid or biocompatible (preferably ophthalmically compatible) salts thereof. More preferably, an α-oxo-multi-acid is citric or malic acid or biocompatible (preferably ophthalmically compatible) salts thereof (e.g., sodium, potassium, or the like).

The solution of the present invention preferably contains a buffering agent. The buffering agents maintain the pH preferably in the desired range, for example, in a physiologically acceptable range of about 6 to about 8. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris (Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis(2-ethanesulfonic acid), TES (N-[Tris(hydroxymethyl)methyl]-2-aminoethanesulfonic acid), salts thereof, phosphate buffers, e.g. $Na_2HPO_4$, $NaH_2PO_4$, and $KH_2PO_4$ or mixtures thereof. A preferred bis-aminopolyol is 1,3-bis(tris[hydroxymethyl]-methylamino)propane (bis-TRIS-propane). The amount of each buffer agent is that amount necessary to be effective in achieving a pH of the composition of from about 6.5 to about 7.5. Typically, it is present in an amount of from 0.001% to 2%, preferably from 0.01% to 1%; most preferably from about 0.05% to about 0.30% by weight.

The solutions according to the invention are preferably formulated in such a way that they are isotonic with the lachrymal fluid. A solution which is isotonic with the lachrymal fluid is generally understood to be a solution whose concentration corresponds to the concentration of a 0.9% sodium chloride solution (308 mOsm/kg). Deviations from this concentration are possible throughout.

The isotonicity with the lachrymal fluid, or even another desired tonicity, may be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof. Preferably, the majority of the tonicity of the solution is provided by one or more compounds selected from the group consisting of non-halide containing electrolytes (e.g., sodium bicarbonate) and non-electrolytic compounds. The tonicity of the solution is typically adjusted to be in the range from about 200 to about 450 milliosmol (mOsm), preferably from about 250 to 350 mOsm.

A packaging solution of the invention can optionally include a viscosity-enhancing polymers, which can be a water soluble cellulose-derived polymer, a water-soluble polyvinylalcohol (PVA), or combination thereof. Examples of useful cellulose-derived polymers include without limitation cellulose ethers. Exemplary preferred cellulose ethers are methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof. More preferably, a cellulose ether is hydroxyethyl cellulose (HEC), hydroxypropylmethyl cellulose (HPMC), and mixtures thereof. The cellulose ether is present in the composition in an amount of preferably from about 0.1% to about 1% by weight, based on the total amount of the packaging solution.

In accordance with the invention, the solution can further comprises mucin-like materials, ophthalmically beneficial materials, and/or surfactants.

Exemplary mucin-like materials include without limitation polyglycolic acid and polylactides. A mucin-like material can be used as guest materials which can be released continuously and slowly over extended period of time to the ocular surface of the eye for treating dry eye syndrome. The mucin-like material preferably is present in effective amounts.

Exemplary ophthalmically beneficial materials include without limitation 2-pyrrolidone-5-carboxylic acid (PCA), amino acids (e.g., taurine, glycine, etc.), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

Surfactants can be virtually any ocularly acceptable surfactant including non-ionic, anionic, and amphoteric surfactants. Examples of preferred surfactants include without limitation poloxamers (e.g., Pluronic® F108, F88, F68, F68LF, F127, F87, F77, P85, P75, P104, and P84), poloamines (e.g., Tetronic® 707, 1107 and 1307, polyethylene glycol esters of fatty acids (e.g., Tween® 20, Tween® 80), polyoxyethylene or polyoxypropylene ethers of $C_{12}$-$C_{18}$ alkanes (e.g., Brij® 35), polyoxyethyene stearate (Myrj® 52), polyoxyethylene propylene glycol stearate (Atlas® G 2612), and amphoteric surfactants under the trade names Mirataine® and Miranol®.

A lens can be prepared according to any methods known to a person skilled in the art from a hydrogel lens-forming formulation. A "hydrogel lens-forming formulation" or "hydrogel lens-forming material" refers to a polymerizable composition which can be cured (i.e., polymerized and/or crosslinked) thermally or actinically to obtain a crosslinked/polymerized polymeric material. Lens-forming materials are well known to a person skilled in the art. Typically a lens forming material comprises polymerizable/crosslinkable components, for example, such as, monomers, macromers, prepolymers, or combinations thereof, as known to a person skilled in the art. A lens-forming material can further include other components, such as non-crosslinkable hydrophilic polymers (i.e., leachable polymeric lubricants), an initiator (e.g., a photoinitiator or a thermal initiator), a visibility tinting agent, UV-blocking agent, photosensitizers, antimicrobial agents (e.g., Ag-nanoparticles), and the like.

Examples of lens making include without limitation, cast-molding, spin-casting, and lathing. A person skilled in the art will know well how to cast-mold lenses from a lens-forming formulation in molds based on thermal or actinic polymerization.

In accordance with the present invention, a hydrogel lens-forming formulation (or a polymerizable fluid composition) can be a solution or a solvent-free liquid or melt at a temperature below 60° C.

In accordance with the invention, leachable lubricants are non-crosslinkable hydrophilic polymers (i.e. without anctinically-crosslinkable groups) having no charges. Any suitable non-charged hydrophilic polymers can be used so long as they are compatible with the lens-forming material (i.e., can produce optically clear contact lenses). Exemplary non-crosslinkable (i.e. without anctinically-crosslinkable groups) hydrophilic polymers include, but are not limited to, polyvinyl alcohols (PVAs), polyamides, polyimides, polylactone, a homopolymer of a vinyl lactam, a copolymer of at least one vinyl lactam in the presence or in the absence of one or more hydrophilic vinylic comonomers, alkylated polyvinylpyrrolidones, a homopolymer of acrylamide or methacrylamide, a copolymer of acrylamide or methacrylamide with one or more hydrophilic vinylic monomers, polyethylene oxide (PEO)), a polyoxyethylene derivative, poly-N—N-dimethylacrylamide, polyacrylic acid, poly 2 ethyl oxazoline, heparin polysaccharides, polysaccharides, and mixtures thereof.

The number-average molecular weight $M_n$ of the hydrophilic polymer is preferably from 10,000 to 500,000, more preferably from 20,000 to 200,000.

Examples of polyvinylpyrrolidone (PVP) include without limitation those polymer characterized by molecular weight grades of K-15, K-30, K-60, K-90, K-120, and the likes.

Examples of copolymers of n-vinylpyrrolidone with one ore more vinylic monomers includes without limitation vinylpyrrolidone/vinylacetate copolymers, vinylpyrrolidone/dimethylaminoethylmethacrylate copolymers (e.g., Copolymer 845, Copolymer 937, Copolymer 958 from ISP Corporation), vinylpyrrolidone/vinylcaprolactam/dimethylaminoethylmethacrylate copolymer.

Examples of alkylated pyrrolidones includes without limitation the family of GANEX® Alkylated pyrrolidone from ISP Corporation.

A suitable polyoxyethylene derivative is, for example, n-alkylphenyl polyoxyethylene ether, n-alkyl polyoxy-ethylene ether (e.g., TRITON®), polyglycol ether surfactant (TERGITOL®), polyoxyethylenesorbitan (e.g., TWEEN®), polyoxyethylated glycol monoether (e.g., BRIJ®, polyoxylethylene 9 lauryl ether, polyoxylethylene 10 ether, polyoxylethylene 10 tridecyl ether), or a block copolymer of ethylene oxide and propylene oxide.

Examples of block copolymers of ethylene oxide and propylene oxide include without limitation poloxamers and poloxamines, which are available, for example, under the tradename PLURONIC®, PLURONIC-R®, TETRONIC®, TETRONIC-R® or PLURADOT®. Poloxamers are triblock copolymers with the structure PEO-PPO-PEO (where "PEO" is poly(ethylene oxide) and "PPO" is poly(propylene oxide).

A considerable number of poloxamers is known, differing merely in the molecular weight and in the PEO/PPO ratio; Examples of poloxamers include 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407. The order of polyoxyethylene and polyoxypropylene blocks can be reversed creating block copolymers with the structure PPO-PEO-PPO, which are known as PLURONIC-R® polymers.

Poloxamines are polymers with the structure (PEO-PPO)$_2$-N—(CH$_2$)$_2$—N-(PPO-PEO)$_2$ that are available with different molecular weights and PEO/PPO ratios. Again, the order of polyoxyethylene and polyoxypropylene blocks can be reversed creating block copolymers with the structure (PPO-PEO)$_2$-N—(CH$_2$)$_2$—N-(PEO-PPO)$_2$, which are known as TETRONIC-R® polymers.

Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available under the tradename PLURADOT®.

Non-crosslinkable PVAs of all kinds, for example those with low, medium or high polyvinyl acetate contents may be employed. In addition, the PVAs used may also comprise small proportions, for example up to 20%, preferably up to 5%, of copolymer units as mentioned before. The use of non-reactive PVAs with a contents of polyvinyl acetate units of less than 20%, preferably lower than 16%, is preferred.

The non-crosslinkable polyvinyl alcohols employed in the present invention are known and are commercially available, for example under the brand name Mowiol® from KSE (Kuraray Specialties Europe).

It is understood that the addition of the leachable lubricants into the lens formulation should have no significantly adverse effects on the optical transparency of the resultant lenses. The leachable lubricants can be the same polymers having different molecular weights or different polymers having different molecular weights.

The present invention, in another aspect, provides a process for making a soft contact lens capable of easing wearer's initial discomfort. The method of the invention comprises the steps of: a) packaging a hydrogel contact lens in a container containing a packaging solution, wherein the packaging solution comprises a homopolymer or copolymer of vinylpyrrolidone, wherein the homopolymer or copolymer is present in an amount sufficient to provide the packaging solution a viscosity of up to about 5.0 centipoises, preferably up to about 4.0 centipoises, even more preferably up to about 3.0 centipoises, most preferably from about 1.2 centipoises to about 2.5 centipoises at 25° C.; glycerin or a polyethylene glycol having an average molecular weight of about 600 or less; and one or more buffering agents in an amount sufficient to provide the solution a pH of from about 6.0 to 8.0, wherein the packaging solution has an osmolality of from about 200 to about 450 mOsm/kg; and b) sterilizing the hydrogel contact lens in the package to obtain the soft contact lens.

Above described various embodiments and preferred embodiments of packaging solutions, hydrogel lens-forming formulations (lens-forming materials), leachable lubricants, packages, sealing and sterilization, and the others can be used in this aspect of the invention.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Example 1

Lens Packaging Solutions

Copolymer 845 is obtained from ISP and PEG 400 (Sentry Carbowax 400) is obtained from Dow. Solutions are prepared by dissolving various components in 1 L of water as shown in Table 1. Where HEC is used as one of the components, the solution is prepared at about 80° C. to dissolve HEC.

TABLE 1

|  | I | II | III | IV |
|---|---|---|---|---|
| NaCl (% by weight) | 0.5 | 0.65 | 0.56 | 0.41 |
| NaH$_2$PO$_4$•H$_2$O (% by weight) | 0.77 | 0.77 | 0.77 | 0.77 |
| Na$_2$HPO$_4$•7H$_2$O (% by weight) | 0.48 | 0.48 | 0.48 | 0.48 |
| Copolymer 845 (% by weight) |  | 1.0 | 1.0 | 1.0 |
| HEC (% by weight) | 0.15 |  |  |  |
| PEG 400 (% by weight) | 0.5 | 1.0 | 2.0 | 1.0 |

Characterization of the Packaging Solution

Advanced Micro-osmometer Model 3300 is used to determine the osmolarity of each packaging solution (averaged over two independent experiment results for each packaging solution). The viscosity of a packaging solution is obtained by averaging three measurements made at three different speeds (3 rpm, 6 rpm and 12 rpm) with the Brookfield Viscometer. The pH value of each packaging solution is determined with Fisher Acumet 25 pH meter (averaged over two independent experiment results for each packaging solution). The results are reported in Table 2.

TABLE 2

|  | I | II | III | IV |
|---|---|---|---|---|
| pH | 7.23 | 7.16 | 7.16 | 7.23 |
| Osmolarity (mOsm) | 292 | 319 | 334 | 308 |
| Viscosity (centipoises) | 3.32 | 1.61 | 1.41 | 1.31 |

Example 2

Cytotoxicity Evaluation

Each packaging solution prepared in Example 1 are tested for cytotoxicity using L-929 (L929) murine fibroblastic cells following 24 hours exposure time points. Alamar Blue Assay (AB) and neutral red uptake and release assay (NRUR) are used to determine the solution cytotoxicity. Neat solutions of the test sample are diluted 1:1, 1:3 and 1:7 (50, 25 and 12.5% final concentration of the neat solution) across a 96 well plate format and exposed to the cell monolayer for a period of 24 hours. For this test, cells grown under controlled conditions are monitored for their viability to survive and grow following initial exposure and incubation with the test solutions, as compared to controls. BAK at 10 ppm is used as a positive control.

The packaging solution I exhibits viability percentages of 83%, 87% and 93% for 50%, 25% and 12.5% test solutions respectively for the AB method at 24 hours exposure for L929 cells and also exhibits viability percentages of 92%, 98% and 97% for 50%, 25% and 12.5% test solutions respectively for the NRUR method at 24 hours exposure for L929 cells.

The packaging solution II exhibits viability percentages of 86%, 92% and 94% for 50%, 25% and 12.5% test solutions respectively for the AB method at 24 hours exposure for L929 cells and also exhibits viability percentages of 99%, 101% and 101% for 50%, 25% and 12.5% test solutions respectively for the NRUR method at 24 hours exposure for L929 cells.

The packaging solution III exhibits viability percentages of 90%, 92% and 94% for 50%, 25% and 12.5% test solutions respectively for the AB method at 24 hours exposure for L929 cells and also exhibits viability percentages of 103%, 102% and 97% for 50%, 25% and 12.5% test solutions respectively for the NRUR method at 24 hours exposure for L929 cells.

The packaging solution IV exhibits viability percentages of 88%, 96% and 94% for 50%, 25% and 12.5% test solutions respectively for the AB method at 24 hours exposure for L929 cells and also exhibits viability percentages of 85%, 98% and 98% for 50%, 25% and 12.5% test solutions respectively for the NRUR method at 24 hours exposure for L929 cells.

The results show that all packaging solutions prepared in Example 1 are considered non-cytotoxic.

Example 3

Solution Preparations

Various solutions are prepared by dissolving various components in PBS saline as shown in Table 3. Each solution is prepared at about 80° C. to dissolve HPMC. Viscosity, pH and osmolarity is measured according to the procedures described in Example 1 and reported in Table 3

TABLE 3

|  | Y1 | Y2 | Y3 | Y4 |
| --- | --- | --- | --- | --- |
| HPMC (% by weight) | 0.15 | 0.15 | 0.15 | 0.15 |
| PEG400 (% by weight) |  | 1.0 |  | 1.0 |
| Copolymer 845 (% by weight) |  |  | 1.0 | 1.0 |
| Sodium citrate (% by weight) |  | 0.294 |  | 0.294 |
| pH | 7.2 | 7.2 | 7.2 | 7.2 |
| Osmolarity (mOsm) | 300 | 299 | 299 | 298 |
| Viscosity (centipoises) | 2.85 | 2.76 | 3.72 | 4.12 |

Lens Packaging

O2OPTIX™ lenses are packaged in blister packages containing a packaging solution (one of Y1, Y2, Y3, and Y4), sealed and autoclaved.

Lenses Characterization

There is no significant changes in the ion permeability, oxygen permeability, reflective index, light transmission, water content, modulus of lenses packaged in either of buffered saline (control), Y1, Y2, Y3, and Y4 packaging solutions. All lenses packaged in the tested packaging solution pass cytotoxic test. The water contact angles (averaged over measurements of three lenses), lipid uptakes, and protein uptakes of lenses packaged in a packaging solution of the invention is reported in the Table.

|  | Packaging Solution | | | | |
| --- | --- | --- | --- | --- | --- |
|  | PBS* | Y1 | Y2 | Y3 | Y4 |
| Water contact angle (degrees) | 49 | 36 | 28 | 30 | 33 |
| Lipid uptake (μg/lens) | 1.3 ± 1.2 | 1.1 ± 0.6 | 4.3 ± 2.2 | 1.2 ± 0.3 | 2.1 ± 0.9 |
| Protein uptake (μg/lens) | 6.1 ± 4.8 | 5.0 ± 1.6 | 11.3 ± 4.3 | 2.1 ± 2.1 | 8.0 ± 3.8 |

Example 4

Commercially available Night & Day lenses along with Acuvue Advance and O2Optix are removed from packaging saline, rinsed three times with a packaging solution (listed below) and then soaked overnight in the packaging solution. The following day the lenses are placed in a fresh 24 well plate with 10 μg/ml phosphotidylethanolamine for another overnight soak. After 24 hours the lenses are moved from 34.5 degrees Celsius incubation and aluminum foil, buffer exchanged three times, placed in fresh 24 well plate with 1 ml of phosphate buffered saline (PBS) and read on the Victor II Wallac.
  1. 1% Aminocoat
  2. 0.25% HEC in PBS
  3. 0.5% Copolymer 845
  4. 2% PVP in PBS
  5. 0.1% HEC and 1% PVP in PBS
  6. 1% PEG 400 and 2% PVP in PBS
  7. 1% PEG 400 and 2% PVA in PBS
  8. 0.5% PEG 400 and 1% K90 PVP in PBS
  9. 0.5% PEG 400 and 2% K90 PVP in PBS
  10. 0.25% PEG 400 and 1% K90 in PBS
  11. 0.25% PEG 400 and 2% K90 PVP in PBS
  12. 0.5% Copolymer 845 with 0.5% Aminocoat in PBS
  13. 0.5% Copolymer 845 with 0.5% PEG 400 in PBS
  14. 0.1% Hydroxypropyl Guar Gum in PBS
  15. Control standard PBS The lenses are soaked in fluorescently tagged phosphotidylethanolamine and therefore readings for fluorescence after being read on the standard curve provided μg/lens counts. Packaging solutions 3, 4, 8, 9, 10 & 11 significantly decreased lipid fouling to all tested silicone hydrogel lenses. All but one of these formulations contained PVP as opposed to Copolymer 845 (FIG. 1).

A standard curve is prepared using a 24-well plate with the curves respective lens type. The standard curve ranged from 10 μg/ml-0 μg/ml in PBS at pH 7.2. Three lenses of each Night & Day, Acuvue Advance & O2Optix are soaked in 10 ug/ml FITC-phosphotidylethanolamine for 24 hours, incubating at 34.5° C. and rocking in complete dark. Once complete lenses are buffer-exchanged 3 times in PBS and then placed in a fresh 24 well plate with 1 ml PBS and read on the Wallac in parallel with each lenses associated standard curve. From these absorbance counts the actual μg/lens counts are calculated.

Example 5

A packaging solution (listed below) is used in an imbibed production process in which lenses are "imbibed" with the packaging solution by using the packaging solution as the hydrating solution for the dry lenses after plasma treatment as well as for lens wet inspection. For the imbibed production process, the packaging solution is are also used for the fill saline (i.e., in the lens package).

1P. 2% Kollidon K90 added to the package saline
2P. 1% Copolymer 845 added to the package saline
3P. Night & Day control lenses packaged in standard production line saline
4P. Dry lenses after plasma treatment imbibed and packaged in 2% Kollidon K90
5P. Dry lenses after plasma treatment imbibed and packaged in 1% Copolymer 845
6P. 0.25% PEG 4000/1% Kollidon K90 added to the package saline
7P. 0.5% Copolymer 845/0.5% PEG 400 added to the package saline
8P. Dry lenses after plasma treatment imbibed and packaged in 0.25% PEG 4000/1% Kollidon K90
9P. Dry lenses after plasma treatment imbibed and packaged in 0.5% Copolymer 845/0.5% PEG 400

Figure 2:
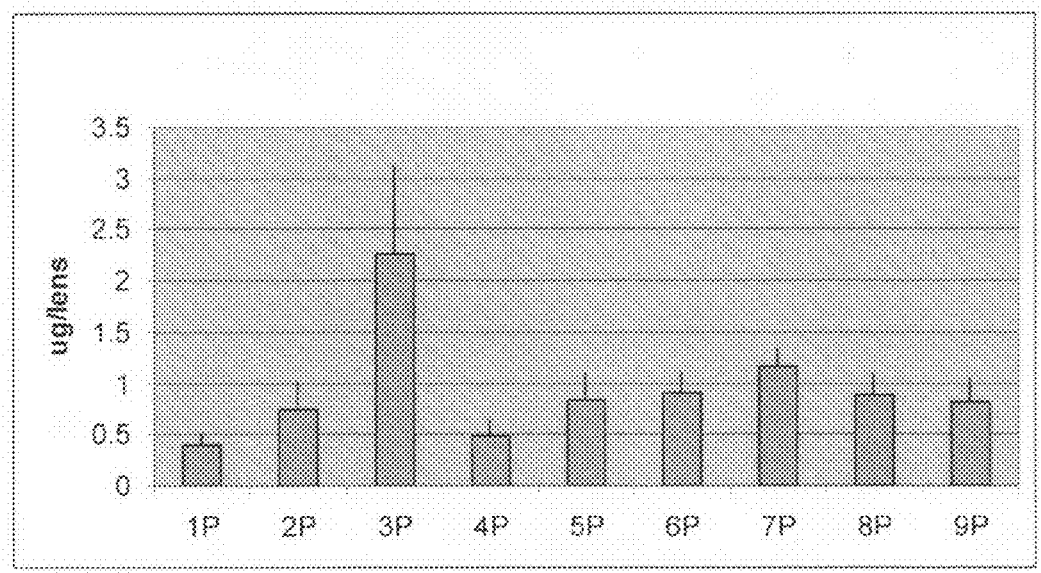
FIG. 2 shows effects of hydrating and storing silicone hydrogel lenses ($O_2$OPTIX) in a packaging solution upon in vitro lipid fouling.

As in the previous study (Example 4), lenses are soaked in fluorescently tagged phosphotidylethanolamine and therefore readings for fluorescence after being read on the standard curve provided μg/lens counts. All lenses showed significantly decreased lipid adsorption (FIG. 2).

A standard curve is prepared using a 24-well plate. Each well containing the lens under investigation to negate any autofluorecense. The standard curve ranged from 10 μg/ml-0.5 μg/ml in PBS at pH 7.2. Five lenses from each group are soaked in 10 μg/ml FITC-phosphotidylethanolamine for 24 hours, rocking at 34.5° C. wrapped in aluminum foil. After incubation lenses are buffer exchanged 3 times in PBS and read on the Victor II Wallac in parallel with each lenses associated standard curve. From these raw counts the actual μg/lens counts are calculated.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

The invention claimed is:

1. An ophthalmic product, comprising a sealed and sterilized package which include a packaging solution and a soft hydrogel contact lens immersed in the packaging solution, wherein the packaging solution includes:
a copolymer of vinylpyrrolidone and at least one amino-containing vinylic monomer, wherein the amino-containing vinylic monomer is selected from the group consisting of alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, and N-vinylalkylamide having 3-10 carbon atoms, wherein the copolymer of vinylpyrrolidone is present in an amount sufficient to provide the packaging solution a viscosity of up to about 5.0 centipoises at 25° C., wherein the copolymer of vinylpyrrolidone has a molecular weight sufficiently large to form a cushion layer on the soft hydrogel contact lens;
a polyethylene glycol having an average molecular weight of about 600 or less;
an α-oxo-multi-acid or salt thereof in an amount sufficient to have a reduced susceptibility to oxidation degradation of the polyethylene glycol in the packaging solution; and
one or more buffering agents in an amount sufficient to provide the solution a pH of from about 6.0 to 8.0, wherein the packaging solution has an osmolality of from about 200 to about 450 mOsm/kg.

2. The ophthalmic product of claim 1, wherein the hydrogel contact lens is a silicone hydrogel contact lens.

3. The ophthalmic product of claim 1, wherein the amino-containing vinylic monomer is dimethylaminoethylmethacrylate or dimethylaminoethylacrylate.

4. The ophthalmic product of claim 1, wherein the packaging solution has a viscosity of up to about 3.0 centipoises at 25° C.

5. The ophthalmic product of claim 1, wherein the packaging solution comprises a polyethylene glycol having an average molecular weight of about 600 or less.

6. The ophthalmic product of claim 1, wherein the α-oxo-multi-acid is selected from the group consisting of citric acid, 2-ketoglutaric acid, and malic acid.

7. The ophthalmic product of claim 1, wherein the α-oxo-multi-acid is citric acid.

8. The ophthalmic product of claim 1, wherein hydrogel contact lens includes one or more leachable lubricant therein.

9. The ophthalmic product of claim 2, wherein the packaging solution comprises glycerin.

10. The ophthalmic product of claim 2, wherein the packaging solution comprises a polyethylene glycol having an average molecular weight of about 600 or less.

11. The ophthalmic product of claim 9, wherein the amino-containing vinylic monomer is dimethylaminoethylmethacrylate or dimethylaminoethylacrylate.

12. The ophthalmic product of claim 10, wherein the amino-containing vinylic monomer is dimethylaminoethylmethacrylate or dimethylaminoethylacrylate.

13. The ophthalmic product of claim 11, wherein the packaging solution has a viscosity of up to about 3.0 centipoises at 25° C.

14. The ophthalmic product of claim 12, wherein the packaging solution has a viscosity of up to about 3.0 centipoises at 25° C.

15. The ophthalmic product of claim 13, wherein the α-oxo-multi-acid is selected from the group consisting of citric acid, 2-ketoglutaric acid, and malic acid.

16. The ophthalmic product of claim 14, wherein the α-oxo-multi-acid is selected from the group consisting of citric acid, 2-ketoglutaric acid, and malic acid.

17. The ophthalmic product of claim 13, wherein the α-oxo-multi-acid is citric acid.

18. The ophthalmic product of claim 14, wherein the α-oxo-multi-acid is citric acid.

* * * * *